United States Patent [19]

Nagamatsu et al.

[11] Patent Number: 5,442,121
[45] Date of Patent: Aug. 15, 1995

[54] PROCESS FOR PRODUCING N,N-DISUBSTITUTED AMINOPHENOL

[75] Inventors: Shigeki Nagamatsu; Tomohiro Arase; Masaaki Yasuda, all of Yamaguchi, Japan

[73] Assignee: Mitsui Petrochemical Industries Ltd., Tokyo, Japan

[21] Appl. No.: 335,744

[22] PCT Filed: Mar. 17, 1994

[86] PCT No.: PCT/JP94/00424

§ 371 Date: Nov. 15, 1994

§ 102(e) Date: Nov. 15, 1994

[87] PCT Pub. No.: WO94/21594

PCT Pub. Date: Sep. 29, 1994

[30] Foreign Application Priority Data

Mar. 19, 1993 [JP] Japan ................... 5-060075

[51] Int. Cl.$^6$ ............................. C07C 209/02
[52] U.S. Cl. .................... 564/398; 564/395; 564/443; 564/468
[58] Field of Search ............... 564/395, 398, 468, 443, 564/403

[56] References Cited

U.S. PATENT DOCUMENTS

| 4,588,841 | 5/1986 | Morellet et al. ............. 564/443 |
| 4,757,144 | 7/1988 | Okabe et al. ............... 544/404 |
| 4,960,432 | 10/1990 | Junino et al. ............... 8/411 |

FOREIGN PATENT DOCUMENTS

| 55-105648 | 8/1980 | Japan . |
| 56-73048 | 6/1981 | Japan . |
| 61-7239 | 1/1986 | Japan . |
| 62-258346 | 4/1986 | Japan . |
| 62-292747 | 6/1986 | Japan . |
| 62-5416 | 2/1987 | Japan . |
| 63-253056 | 10/1988 | Japan . |
| 3099042 | 9/1989 | Japan . |

*Primary Examiner*—Allen J. Robinson
*Assistant Examiner*—Brian M. Burn
*Attorney, Agent, or Firm*—Birch, Stewart, Kolasch & Birch

[57] ABSTRACT

A process for producing N,N-disubstituted aminophenol which comprises the steps of:

obtaining a reaction mixture containing N-substituted aminophenol by reacting a dihydric phenol and an amine;

subjecting said reaction mixture to heat treatment so as to thermally decompose quaternary ammonia salt contained in said reaction mixture into a dihydric phenol and an amine, and removing at least said amine by distillation;

separating high-boiling impurities by distillation to separate N-substituted aminophenol; and subjecting said separated N-substituted aminophenol to reduction alkylation using an aldehyde compound.

According to the present invention, high-purity N,N-disubstituted aminophenol can be obtained in a high yield at high selectivity, and a reduction catalyst can be used repeatedly because its activity can be maintained at a high level and yet it can retain high activity for a long period of time.

3 Claims, No Drawings

PROCESS FOR PRODUCING N,N-DISUBSTITUTED AMINOPHENOL

This application is a 371 of PCT/JP94/00424, filed Mar. 17, 1994.

DETAILED DESCRIPTION OF THE INVENTION

1. Field of the Invention

This invention relates to a process for producing N,N-disubstituted aminophenol and, more specifically, to a process for producing high-purity N,N-disubstituted aminophenol at a high yield by aminating and alkylating a dihydric phenol. N,N-disubstituted aminophenol is a valuable compound as an intermediate for producing dyes for heat-sensitive recording papers and fluorescent dyes.

2. Prior Art

Known prior art processes for producing N,N-disubstituted aminophenol include:

(1) a process which comprises reacting a dihydric phenol with a primary amine in the presence of an acid catalyst (first-stage reaction) and alkylating the resulting N-substituted aminophenol with dialkylsulfuric acid or a halogenated alkyl such as alkyl chloride, alkyl bromide or alkyl iodide (second-stage reaction); and (2) a process which comprises aminating a dihydric phenol with ammonia to produce an aminophenol, separating and purifying the aminophenol, and adding aldehydes stepwise to the aminophenol in the copresence of a reduction catalyst, an organic carboxylic acid, an organic solvent and hydrogen for reduction alkylation.

However, in the process (1), an inorganic acid by-produced in the second-stage alkylation reaction must be neutralized and, hence, a large volume of waste water is produced. When bromine or iodine is used as a halogen, recovery of these halogens is necessary because they are expensive, and the industrial production process becomes complicated. Further, when dialkylsulfuric acid and a halogenated alkyl are used, alkylation of an OH group takes place and a quaternary salt is by-produced by aminophenol and alkylsulfuric acid, with a consequence that the yield of N,N-disubstituted aminophenol decreases and the purification step becomes complicated.

In the process (2), due to a low yield in the step of aminating the dihydric phenol with ammonia, a large amount of the dihydric phenol as a source material remains in the reaction mixture and as a result a complicated step for separating and purifying the resulting aminophenol is required.

A process for producing N-substituted aminophenol by reacting a dihydric phenol with ammonia, a primary amine or a secondary amine in the absence of a catalyst is disclosed in Japanese Patent Publication No. 5416/1987 and Japanese Patent Laid-open Publication No. 99042/1991.

Further, a process for obtaining N,N-disubstituted aminophenol by a reduction alkylation reaction between N-substituted aminophenol and aldehyde in an organic solvent in the presence of hydrogen and a reduction catalyst is disclosed in Japanese Patent Laid-Open Publication Nos.258346/1987 and 292747/1987. According to this process, there can be separated N,N-disubstituted aminophenol purified by distillation after the reduction catalyst has been separated from the reaction mixture after the reaction. With this process, N,N-disubstituted aminophenol can be obtained at high conversion and at high selectivity as far as high-purity N-substituted aminophenol is used as a source material.

However, when a dihydric phenol is used as a starting material and amination and reduction alkylation reactions are carried out to obtain N,N-disubstituted aminophenol in accordance with the two reactions disclosed in the aforementioned Japanese Patent Publications, the objective N,N-disubstituted aminophenol cannot be obtained at a high yield when the catalyst is used several times because the activity of the reduction catalyst lowers in the reduction alkylation step and the catalyst has a short life.

Problem to Be Solved by the Invention

It is therefore a first object of the invention to provide an industrially advantageous process for obtaining N,N-disubstituted aminophenol at high conversion and at high selectivity in a series of steps for obtaining N,N-disubstituted aminophenol from a dihydric phenol as a starting material.

It is a second object of the invention to provide a process in which the activity of a reduction catalyst does not deteriorate and is maintained at a high level in the reduction alkylation reaction step in the above series of steps.

It is a third object of the invention to provide a process in which the activity of a reduction catalyst can be maintained satisfactorily high even when the catalyst is used repeatedly in the above reduction alkylation reaction step, namely a process for obtaining N,N-disubstituted aminophenol at high conversion and at high selectivity even when the reduction catalyst is used repeatedly.

MEANS FOR SOLVING THE PROBLEM

According to studies conducted by the present inventors, it was found that the objects and advantages of the present invention can be achieved by the following five steps (1) to (5):

(1) step I in which a reaction mixture containing N-substituted aminophenol represented by the following formula (2)

wherein $R^1$ is an alkyl group having 1 to 6 carbon atoms or a cycloalkyl group having 4 to 8 carbon atoms is obtained by reacting a dihydric phenol with a primary amine represented by the following formula (1)

wherein $R^1$ is the same as defined in formula (2);

(2) step II in which a quaternary ammonia salt represented by the following formula (3)

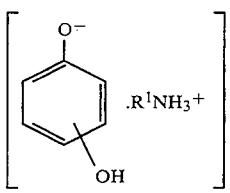

wherein $R^1$ is the same as defined in the formula (2) and inevitably present in said reaction mixture obtained in the previous step I is subjected to a heat treatment to decompose the quaternary ammonia salt into a dihydric phenol and the primary amine of the formula (1) and at least the substantial amount of the primary amine is removed from said reaction mixture;

(3) step III in which N-substituted aminophenol represented by the formula (2) is separated from said reaction mixture obtained in the previous step II by distillation;

(4) step IV in which N,N-disubstituted aminophenol represented by the following formula (5)

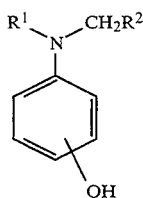

wherein $R^1$ is the same as defined in the formula (2) and $R^2$ is an alkyl group having 1 to 5 carbon atoms or a cycloalkyl group having 4 to 8 carbon atoms, is obtained by reacting N-substituted aminophenol obtained in the previous step III with an aldehyde compound represented by the following formula (4)

$$R^2CHO \qquad (4)$$

wherein $R^2$ is the same as defined in the formula (5) in an organic solvent and in the presence of a reduction catalyst in a hydrogen gas atmosphere; and (5) step V in which N,N-disubstituted aminophenol is isolated from a reaction mixture obtained in the previous step IV.

The process of the present invention is explained in detail hereinunder.

In the process of the present invention, first, the step I is a step in which a dihydric phenol is reacted with a primary amine. In this instance, preferable examples of the dihydric phenol include resorcinol and hydroquinone. The primary amine is a compound represented by the formula (1). In the formula, $R^1$ is an alkyl group having 1 to 6 carbon atoms or a cycloalkyl group having 4 to 8 carbon atoms. The alkyl group having 1 to 6 carbon atoms may be straight-chain or branched-chain. Examples of the primary amine include methylamine, ethylamine, n-propylamine, isopropylamine, n-butylamine, sec-butylamine, tert-butylamine, amylamine, isoamylamine, hexylamine, cyclobutylamine, cyclopentylamine, cyclohexylamine, cycloheptylamine, cyclooctylamine and the like.

In the amination reaction of the step I, the primary amine is used in a proportion of 0.4 to 1.8 mols, preferably 0.7 to 1.5 mols, based on one mol of the dihydric phenol.

The amination reaction in the step I can be carried out in either the presence or absence of a reaction medium. When a reaction medium is used, examples of the reaction medium include inert media such as water; aromatic hydrocarbons such as benzene, toluene and xylene; alicyclic hydrocarbons such as cyclohexane; and polar media such as N,N-dimethylformamide, phenol, -p-chlorophenol, o,o'-biphenol and p,p'-biphenol.

The reaction is carried out in an inert gas atmosphere such as argon, helium or nitrogen, preferably in a nitrogen gas atmosphere. Further, the reaction is suitably carried out at a temperature of 150° to 250° C., preferably 160° to 220° C. under an initial pressure (gauge pressure) of normal pressures to 4 kg/cm².

In the amination reaction of the aforementioned step I, the objective N-substituted aminophenol represented by the formula (1) is mainly produced, but quaternary ammonia salt represented by the following formula (3)

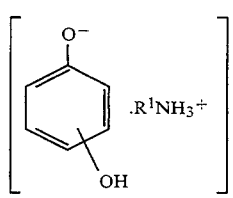

wherein $R^1$ is the same as defined in the formula (2) is inevitably present in the reaction mixture, as is apparent from the Reference Examples to be described below.

In the step II of the process of the present invention, it is important to thermally decompose the quaternary ammonia salt of the formula (3) in the reaction mixture obtained in the step I to convert it into a dihydric phenol and a primary amine of the formula (1). Thereby, in the distillation separation of the N-substituted aminophenol from the reaction mixture in the step I, the inclusion of the primary amine can be minimized. In other words, the distillation separation of N-substituted aminophenols represented by the formula (2) from the reaction mixture in the step I is generally carried out in a continuous twin column and in a batch manner, but it is difficult to separate the quaternary ammonia salt of the formula (3) from N-substituted aminophenols of the formula (2) in the distillation step. Since the quaternary ammonia salt is partly decomposed in the distillation step to produce a primary amine, it is also contained in the N-substituted aminophenol of the formula (2). Therefore, in this case, the quaternary ammonia salt and primary amine contained in the N-substituted aminophenol poisons the reduction catalyst to lower its activity in the reduction alkylation step (step IV), and reduces the reaction yield of the objective compound and increases the formation of impurities in the reduction alkylation reaction. When the catalyst is used repeatedly, deterioration in the activity of the catalyst proceeds and the yield is lowered, thus shortening the life of the catalyst. As a result, an industrially stable operation cannot be attained and catalyst costs increase.

According to the process of the present invention such problems can be avoided by carrying out the steps II and III before the reduction alkylation step IV as described above. In the step II, it is advantageous that the operation of thermally decomposing the quaternary ammonia salt of the formula (3) into a dihydric phenol and a primary amine is carried out while distilling out the produced primary amine together with low-boiling impurities produced by the reaction, or the low-boiling impurities produced by the reaction and the organic solvent. This thermal decomposition operation can be carried out at either an increased or reduced pressure and in either a batch or continuous manner. A heating can or a distillation column is used as an apparatus for thermal decomposition. The thermal decomposition operation is usually carried out at a pressure of 100 mmHg or less, preferably 50 mmHg or less, at a column bottom temperature of 100° to 200° C., preferably 120° to 180° C. With a rise in the column bottom temperature the thermal composition reaction is accelerated, but this also invites an increase in the weight of reaction product and the decomposition of the product, which is not desirable. The thermal decomposition of the step II is carried out under the condition that the presence of quaternary ammonia salt is substantially recognizable.

According to the process of the present invention, in the subsequent step III, N-substituted aminophenols represented by the formula (2) are separated from the reaction mixture by distillation. This distillation can be carried out at either an increased or reduced pressure and in either a continuous or batch manner. The distillation operation of the step III is usually carried out at a column top pressure of 30 mmHg or less, preferably 20 mmHg or less, more preferably 10 mmHg or less. As the pressure increases, the temperature inside the column rises, which induces an increase in the weight of and the decomposition of N-substituted aminophenols and other reaction products, resulting in lowering of the yield and increasing of the amounts of impurities including N-substituted aminophenols in the reaction products.

The N-substituted aminophenols obtained in the step III are subjected to a reduction alkylation reaction, together with the aldehyde compound of the formula (4) in the step IV. This reduction alkylation reaction allows the N-substituted aminophenols of the formula (2) and the aldehyde compound to react in an organic solvent in a hydrogen gas atmosphere in the presence of a reduction catalyst.

It is advantageous to carry out this reduction alkylation of the step IV at a hydrogen pressure of normal pressures to 50 kg/cm$^2$G, preferably normal pressures to 15 kg/cm$^2$G, at a reaction temperature of 5° to 60° C., preferably 10° to 40° C.

The aldehyde compound of the formula (4) used in the present invention is selected from compounds corresponding to the compound of the formula (4) in which $R^2$ is an alkyl group having 1 to 5 carbon atoms or a cycloalkyl group having 4 to 8 carbon atoms. Specific preferable examples of the aldehyde compound include acetaldehyde, propionaldehyde, n-butylaldehyde, isobutylaldehyde, isoamylaldehyde, hexylaldehyde, cyclobutylaldehyde, cyclopentylaldehyde, cyclohexylaldehyde, cycloheptylaldehyde, cyclooctylaldehyde and the like.

These aldehyde compounds are used in a proportion of 0.7 to 1.5 mols, preferably 0.9 to 1.3 mols, based on one mol of N-substituted aminophenol.

Examples of the reduction catalyst used in the step IV include ones in which metals of the group VIII of the periodic table such as Pd, Pt, Rh, Co, Ni and Ru are carried on inert carriers, such as active carbon and alumina. Among them, a reduction catalyst in which Pt is carried on active carbon is preferably used. Examples of the organic solvent used in the present invention include lower aliphatic alcohols such as methanol, ethanol, propanol and butanol. Among them, methanol and ethanol are especially preferred.

After completion of the reduction alkylation reaction in the step IV, depressurization is carried out, the reduction catalyst is separated from the reaction mixture containing N,N-disubstituted aminophenol of the general formula (5) by filtration, and then N,N-disubstituted aminophenol purified by distillation can be isolated.

The separated reduction catalyst can be used again as a reduction catalyst because it maintains sufficient activity. According to the process of the present invention, even after the reduction catalyst is used repeatedly at least ten times, it retains enough activity to be used for industrial application.

EFFECT OF THE INVENTION

As described above, according to the process of the present invention, N-substituted aminophenol, which is obtained by in advance thermally decomposing a quaternary ammonia salt contained in the reaction mixture obtained by the amination reaction between a dihydric phenol and a primary amine, and removing the primary amine by distillation, and then separating high-boiling impurities by a distillation operation, is used in a reduction alkylation reaction thereby to increase the yield from the reduction alkylation reaction and suppress the formation of impurities. Consequently, a high-purity product containing little impurities can be obtained at a high yield and industrially stably. Moreover, as the activity of the reduction catalyst hardly deteriorates and is maintained at a high level even after repeated use, the process of the present invention is industrially advantageous.

EXAMPLES

The present invention is illustrated by the following examples, but the present invention is not intended to be limited by these examples by any means.

In the following examples and comparative examples, the yield and selectivity of N,N-disubstituted aminophenol are calculated from the equations below, respectively.

Yield (%) of N,N-disubstituted aminophenol =

$$\frac{\text{number of mols of N,N-disubstituted aminophenol produced by reaction}}{\text{number of mols of N-substituted aminophenol before reaction}} \times 100$$

Selectivity (%) of N,N-disubstituted aminophenol =

$$\frac{\text{number of mols of N,N-disubstituted aminophenol produced by reaction}}{\text{number of mols of N-substituted aminophenol after reaction}} \times 100$$

Example 1

An autoclave made of SUS316 was charged with 110 parts by weight of resorcinol in a nitrogen atmosphere and closed up tight, and the temperature was elevated to 130° C. to melt resorcinol. When the inner temperature reached 130° C., 36 parts by weight of monoethylamine was supplied to the autoclave over one hour while it was stirred. Thereafter, the temperature was elevated to 170° C. and stirring was continued for 7 hours while maintaining this temperature.

After completion of the reaction, the autoclave was cooled and depressurized, and the reaction mixture was analyzed by gas chromatography. The yield of N-ethyl-m-aminophenol was 64.1 mol %.

The reaction mixture was then transferred to an evaporation can and the pressure and temperature were maintained at 100 mmHg and 140° C., respectively, while the mixture was stirred, so as to carry out 1 hour of thermal decomposition and removal of low-boiling impurities. The low-boiling impurities in the system were removed at a pressure of 15 mmHg, and then the reaction product was removed at a temperature of 190° C. to separate high-boiling impurities. The temperature was 200° C. when recovery of the reaction product was completed. When the thus obtained reaction product was analyzed by gas chromatography, the concentration of monoethylamine contained in the reaction product was 0.2% and the yield of N-ethyl-m-aminophenol was 87.0 wt %.

An autoclave made of SUS316 was charged with 26 parts by weight of N-ethyl-m-aminophenol contained in the reaction product, 72 parts by weight of methanol as an organic solvent, and 2 parts by weight of a Pt catalyst as a reduction catalyst in which 2 wt % of Pt was carried on active carbon in a nitrogen atmosphere, and the inside was replaced with hydrogen under stirring, and then the pressure was elevated to 7 kg/cm$^2$G. 18 Parts by weight of isoamylaldehyde was supplied to the autoclave over 3 hours while the hydrogen pressure and temperature were maintained at a constant level and 30° to 35° C., respectively. Thereafter, while the above pressure and temperature were maintained, stirring was continued for 3 hours.

After completion of the reaction, the autoclave was cooled and depressurized, and the reaction mixture was filtered to separate the reduction catalyst. When the reaction mixture obtained as a filtrate was analyzed by gas chromatography, it was found that the yield of N-ethyl-N-isoamyl-m-aminophenol was 84.7 mol % and its selectivity was 88.7 mol %.

Comparative Example 1

An amination reaction was carried out in the same manner as in Example 1. After low-boiling impurities and high-boiling impurities contained in the reaction mixture were removed by distillation without carrying out thermal decomposition and removal of quaternary ammonia salt, the resulting reaction product was used to carry out a reduction alkylation reaction. Thin-film distillation was first carried out at an evaporation surface temperature of 130° C. under a pressure of 100 mmHg to remove low-boiling impurities. Thereafter, distillation was carried out in a distillation column at a column bottom temperature of 200° C. under a pressure of 10 mmHg to remove high-boiling impurities to obtain a reaction product. The reaction product obtained by distillation was analyzed by gas chromatography. The results show that the concentration of monoethylamine contained in the reaction product was 0.6 wt %.

A reduction alkylation reaction was carried out in the same manner as in Example 1, using the thus obtained reaction product. When the resulting reaction mixture was analyzed by gas chromatography, it was found that the yield of N-ethyl-N-isoamyl-m-aminophenol was 69.8 mol % and its selectivity was 82.6 mol %.

Example 2

An autoclave made of SUS316 was charged with 26 parts by weight of N-ethyl-m-aminophenol in the reaction product obtained in Example 1, 72 parts by weight of methanol as an organic solvent, and the filtered and separated catalyst used in Example 1 and 0.2 parts by weight of a new Pt catalyst in which 2 wt % of Pt was carried on active carbon as reduction catalysts in a nitrogen atmosphere. The inside of the autoclave was replaced with hydrogen under stirring, and the pressure was elevated to 7 kg/cm$^2$G. While the hydrogen pressure and temperature were maintained at a constant level and 30° to 35° C., respectively, 18 parts by weight of isoamylaldehyde was fed to the autoclave over 6 hours. Thereafter, while the above pressure and temperature were maintained, stirring was continued for 3 hours. After completion of the reaction, the autoclave was cooled and depressurized, the reaction mixture was filtered to separate the reduction catalysts, and the reaction mixture obtained as a filtrate was analyzed by gas chromatography. When this operation was performed repeatedly and the catalysts were recycled 8 times, the yield of N-ethyl-N-isoamyl-m-aminophenol was 84 to 87 mol % and its selectivity was 86 to 90 mol %.

Comparative Example 2

A reaction was carried out in the same manner as in Example 2 using the reaction product obtained in Comparative Example 1, and the reaction mixture obtained as a filtrate was analyzed by gas chromatography. When this operation was repeated and the catalyst was recycled 8 times, the yield of N-ethyl-N-isoamyl-m-aminophenol was 64 to 70 mol % and its selectivity was 80 to 82 mol %.

Reference Example (Confirmation of Formation of Quaternary Ammonia Salt)

(1) synthesis and isolation methods;

A test tube was charged with 2.75g of resorcinol and 1.8 g of ethylamine was added to the tube at 15° C. and stirred with a stirrer chip. The temperature of the mixture rose to 35° C. and the mixture became an emulsion.

Nitrogen gas was blown onto this mixture through a capillary tube to remove ethylamine. The mixture was solidified.

The solidified mixture was pulverized using a mortar to prepare a sample for structure analysis.

(2) results of NMR and MASS spectral analysis

As the result of NMR and MASS spectral analysis, it was confirmed that the sample has the following structure.

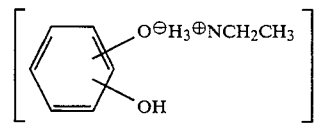

(3) result of melting point measurement

When the melting point of the sample was measured with a differential thermometer (DSC), calorimetric absorption was observed at 86.3° C. and 113° C.

Resorcinol has a melting point of 116° C. ($\alpha$-type) or 110.5° C. and a boiling point of 28.4° C. Ethylamine has a melting point of $-81$° C. and a boiling point of 16.6° C.

(4) result of measurement with thermobalance

It is assumed that the reduction in weight was large at measurement temperatures between 60° and 90° C. and hence decomposition of quaternary ammonia salt starts around 60° C.

We claim:

1. A process for producing N,N-disubstituted aminophenol which comprises:

(1) step I in which a reaction mixture containing an N-substituted aminophenol represented by the following formula (2)

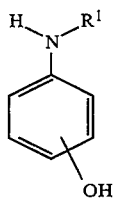  (2)

wherein $R^1$ is an alkyl group having 1 to 6 carbon atoms or a cycloalkyl group having 4 to 8 carbon atoms is obtained by reacting a dihydric phenol with a primary amine represented by the following formula (1)

$$R^1NH_2 \qquad (1)$$

wherein $R^1$ is the same as defined in the formula (2);

(2) step II in which a quaternary ammonia salt represented by the following formula (3)

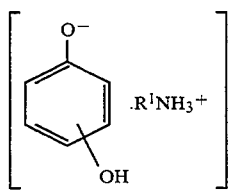  (3)

wherein $R^1$ is the same as defined in the formula (2) and present inevitably in said reaction mixture obtained in the previous step I is subjected to heat treatment to decompose said quaternary ammonia salt into a dihydric phenol and said primary amine of the formula (1) and at least the substantial amount of said primary amine is removed from said reaction mixture;

(3) step III in which N-substituted aminophenol represented by the formula (2) is separated from said reaction mixture obtained in the previous step II by distillation;

(4) step IV in which N,N-disubstituted aminophenol represented by the following formula (5)

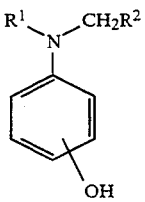  (5)

wherein $R^1$ is the same as in the formula (1) and $R^2$ is an alkyl group having 1 to 5 carbon atoms or a cycloalkyl group having 4 to 8 carbon atoms, is obtained by reacting said N-substituted aminophenol obtained in the previous step III with an aldehyde compound represented by the following formula (4)

$$R^2CHO \qquad (4)$$

wherein $R^2$ is the same as in the formula (5) in an organic solvent and in a hydrogen atmosphere in the presence of a reduction catalyst; and (5) step V in which said N,N-disubstituted aminophenol is isolated from said reaction mixture obtained in the previous step IV.

2. The production process according to claim 1 wherein the reaction in the step IV is carried out in the presence of a reduction catalyst in which a metal of group VIII of the periodic table is carried on an inert carrier.

3. The production process according to claim 1 wherein said reduction catalyst used in the reaction of the step IV is separated and recovered from said reaction mixture for recycling as a reduction catalyst in the reaction of the step IV.

* * * * *